US007006205B2

(12) United States Patent
Agarwal et al.

(10) Patent No.: US 7,006,205 B2
(45) Date of Patent: Feb. 28, 2006

(54) METHOD AND SYSTEM FOR EVENT DETECTION IN PLASMA PROCESSES

(75) Inventors: Ashish Agarwal, Pittsburgh, PA (US); Dimitris Lymberopoulos, San Jose, CA (US)

(73) Assignee: Applied Materials Inc., Santa Clara, CA (US)

( * ) Notice: Subject to any disclaimer, the term of this patent is extended or adjusted under 35 U.S.C. 154(b) by 485 days.

(21) Appl. No.: 10/159,768

(22) Filed: May 30, 2002

(65) Prior Publication Data
US 2003/0223055 A1 Dec. 4, 2003

(51) Int. Cl.
*G01N 21/00* (2006.01)
(52) U.S. Cl. .......................... 356/72; 356/326
(58) Field of Classification Search .............. 356/72, 356/326, 614; 216/60, 67, 59; 438/9, 14, 438/16; 700/48; 706/15, 16, 19
See application file for complete search history.

(56) References Cited

U.S. PATENT DOCUMENTS

| | | | | |
|---|---|---|---|---|
| 5,347,460 A | * | 9/1994 | Gifford et al. | 700/121 |
| 5,711,843 A | * | 1/1998 | Jahns | 156/345.24 |
| 5,841,651 A | * | 11/1998 | Fu | 700/48 |
| 6,101,971 A | * | 8/2000 | Denholm et al. | 118/723 E |

OTHER PUBLICATIONS

Ronald L. Allen, Randy Moor, and Mike Whelan, "Application of neural networks to plasma etch end point detection", *J Vac. Sci Technol*, B 14(1), Jan./Feb. 1996.

Michael D. Baker, Christopher D. Himmel, and Gary S. May, "In-Situ Prediction of Reactive Ion Etch Endpoint Using Neural Networks", *IEEE Transactions on Compoents, Packaging, and Manufacturing Technology*—Part A, vol. 18, No. 3, Sep. 1995.

* cited by examiner

*Primary Examiner*—Gregory J. Toatley, Jr.
*Assistant Examiner*—Roy M. Punnoose
(74) *Attorney, Agent, or Firm*—Dergosits & Noah

(57) ABSTRACT

Plasma events are detected by analyzing the spectral emissions of a plasma process of a substrate. A plasma is monitored by a spectrometer which produces plasma emission data which includes an intensity value for each individual wavelength which is a large quantity of information. The plasma emission data is processed with an algorithm or combination of algorithms to reduce the quantity of the plasma emission data. A peak finding algorithm which identifies the wavelengths of light which are associated with a plasma process allowing the other wavelengths to be ignored. A data reduction algorithm provides a single value representative of the intensity of the emitted light from each peak. A noise reduction algorithm removes noise from the spectral signal by eliminating signals at wavelengths which do not exceed a threshold intensity and do not exceed a threshold wavelength span. The data may also be processed with principal component analysis to further reduce the optical emission data. By reducing the optical emission data, the neural network can provide faster data analysis. The neural network of the inventive system identifies the plasma event after being trained and can control the processing equipment when plasma events are detected.

15 Claims, 12 Drawing Sheets

METHOD AND SYSTEM FOR EVENT DETECTION IN PLASMA PROCESSES

FIELD OF THE INVENTION

The present invention relates generally to the field of plasma processing and, more specifically, the monitoring and characterization of plasma processes.

BACKGROUND OF THE INVENTION

Plasma is used in many industrial processes including semiconductor fabrication. Semiconductor plasma processing typically involves placing a wafer into a plasma processing chamber and exposing the wafer to a plasma for a specific period of time in achieve the desired process. Plasma processing steps commonly used in semiconductor integrated circuit fabrication include, deposition, etching and cleaning. A specific series of plasma processing steps are required to fabricate integrated circuits on a substrate each of which must be properly performed to produce functional integrated circuits on the wafer.

A single wafer may contain thousands of integrated circuits. Thus, when the plasma processing steps are properly performed, a high percentage of functional integrated circuits are produced on the semiconductor wafer. Errors in plasma processing result in defective integrated circuits and a lower percentage of functional integrated circuits are produced on a wafer.

Plasma processing errors may be caused by failing to stop the plasma process at the correct time or at the correct "end point" of the plasma process. For example, in a plasma etching process, two layers of material on the wafer are etched through and the etch end point is ideally immediately after the second layer of material has been etched through. If the etch process is stopped too early, the etch process will not be complete because the second layer is not be completely etched through, leaving excess material at the bottom of the etch. This excess material may cause the associated integrated circuit formed on the wafer to be defective and non-functional. If the plasma etch process continues beyond the etch end point, the underlying layer below the etch layer(s) is also etched. Because devices are formed with very thin layers of material, excessive etching can very easily etch completely through the underlying third layer which may also create a defective and non-functional integrated circuits on the wafer.

To reduce plasma processing errors, the plasma may be monitored so that the end point of a plasma process may be detected. When the end point is detected a control signal may be sent to the processing chamber to stop the plasma process. In some applications, the end point can be detected by monitoring the optical emissions of the plasma.

SUMMARY AND OBJECTS OF THE INVENTION

The present invention characterizes a plasma by monitoring the optical emission during plasma processing with a spectrometer and analyzing optical emission data from the spectrometer with a neural network to determine when plasma events occur. During wafer processing the plasma emits optical wavelengths which represent the specific species in the plasma. An optical spectrometer is exposed to the optical emission of the plasma and converts the optical emission into optical emission data representing the optical amplitude for each wavelength of an optical spectrum.

The optical spectrum of the plasma is graphically illustrated by plotting the wavelengths of the optical emission along the X-axis and the amplitude of each wavelength along the Y-axis. A plasma emission may have about 2,048 distinct wavelengths of light each with a specific intensity. Because the optical emission is related to specific species, the optical spectrum may include various wavelengths which resemble peaks. The amplitude of the peaks is proportional to the concentration of the species in the plasma.

Signals representing the emission amplitude of each wavelength of the plasma's optical spectrum are transmitted from the spectrometer to a neural network. The neural network analyzes the optical spectrum signals and produces a plasma characterization. The characterization indicates the chemical reactions of the plasma. Typically, the end point of a plasma process is detected by changes in the plasma characterization. Thus, when a change in the plasma characteristic is detected by the neural network, the plasma processing chamber controls can be instructed to stop the plasma process.

Neural networks are known devices which have various configurations. The complexity of the neural network may be proportional to the number of inputs, thus a large neural network may be required to process all 2,048 wavelengths of the plasma emission. If the neural network has fewer inputs a less complex neural network may be used and results may be obtained more quickly. It is therefore desirable to reduce the number input signals so that a less complex neural network may be used to characterize the plasma emission. The inventive system utilizes an algorithm or combination of algorithms to reduce the number of inputs to the neural network In an embodiment, a peak finding algorithm is used to reduce the number of neural network input signals representing the optical emission of the plasma. In the optical spectrum of a plasma there are specific wavelengths associated with specific species in the plasma. These wavelengths have high amplitudes and are illustrated as peaks on an optical spectrum. By analyzing only the wavelengths associated with the peaks of the optical spectrum and ignoring the data from other wavelengths the number inputs to the neural network can be reduced without compromising the accuracy of the plasma characterization.

The peak finding algorithm determines which wavelengths associated with amplitude peaks by scanning the plasma emission spectrums for all plasma reactions taking place. The wavelength of a leading edge of an amplitude peak may be detected by a rapid emission amplitude increase and similarly, the trailing edge of the amplitude peak is detected by a rapid decrease in emission amplitude. The peak finding algorithm identifies the peak wavelengths as those wavelengths between the leading and trailing edges of a peak and removes data for all other wavelengths from the optical emission data. By transmitting only emission data for the peak wavelengths to the neural network, substantially fewer signals must be analyzed by the neural network. Because the non-peak wavelengths do not contain information indicative of the plasma process, a less complex neural network may be used without compromising the accuracy of the plasma characterization.

In another embodiment, a data reduction algorithm may further reduce the quantity of optical emission data transmitted to the neural network. The data reduction algorithm reduces the quantity of data transmitted to the neural network complexity and improves the accuracy of the plasma emission data. The data reduction algorithm identifies peak wavelength groups and converts the amplitudes of each group of wavelengths associated with each peak into a single cumulative value. The improved accuracy of the data reduction algorithm is based upon the physical nature of plasma emissions. The concentration of a specific species in a plasma is proportional to the cumulative plasma intensity over a range of wavelengths rather than a single wavelength. The cumulative value represents the "area" under each peak of the optical emission spectrum or the cumulative emission amplitude of the peak. This single cumulative value is a more accurate representation of the concentration of a plasma species than a single intensity value for a single wavelength. By processing the optical spectrum with the peak finding and data reduction algorithms, the number of inputs to the neural network may be reduced from about 2,048 inputs representing all wavelengths in the optical spectrum to approximately 103 inputs.

In an alternative embodiment, a noise reduction algorithm may be used to reduce the number of plasma emission signals transmitted to the neural network. The noise reduction algorithm also scans the emission spectrum and identifies noise signals which have a small wavelength width and low amplitudes. Signals which are identified as noise are removed and so that only wavelengths representing peak data is transmitted to the inputs of the neural network. Again, the number of inputs signals to the neural network is reduced without compromising the accuracy of the characterization.

In yet another embodiment, the optical emission data may be reduced with a principal component analysis (PCA) algorithm. PCA reduces data by extracting information by finding the direction in the input space in which the inputs exhibit the most variation. The PCA algorithm then transforms the number of variables into a smaller number of variable called principal components. The first principal components account for most of the variability in the data. By applying a PCA algorithm, a large number of inputs can be greatly reduced before being analyzed by the neural network. Several data reduction algorithms have been described including: peak finding, noise reduction, data reduction and principal component analysis which may be used in any combination or independently. None of the described data reduction algorithms are mutually exclusive.

Broadly defined, a neural network is a system (hardware or software) which emulates the functions of an animal nervous system with inputs (senses) interconnected to neurons which are analyzed by a central processor (brain). There are various types of neural networks including feed-forward and feedback. In an embodiment, the neural network is a computer program. The neural network includes two or more "levels." Each level includes a plurality inputs, a plurality of neurons and a transfer function. The inputs to the first layer of the neural network include the plasma emission signals. Each input is fed to a neuron which adjusts the value by multiplying the input by a "weight" and adding a correction "bias." The outputs of the neurons are summed and processed by a transfer function which produces one or more output signals for the layer. The output signal(s) of the transfer function are transmitted to the input(s) of other layers. The last layer of the neural network produces a single output which is a characterization of the monitored plasma.

Before a neural network can accurately characterize a plasma emission, it must go through a training process during which the weights and biases of the neurons are set. There several types of neural network training processes including supervised and unsupervised. In supervised training, plasma emission data and the correct plasma characterization are fed to the neural network. The weights and biases of the neurons are then adjusted so that the neural network produces the correct plasma characterization based upon the given plasma inputs. In unsupervised training, the neural network automatically adjusts the weights and biases to correct the output characterizations of the optical emission data in an interactive process. The neural network adjusts the weights and biases of the neurons to more accurately characterize the optical emission data. After the training process is complete the neural network can accurately characterize a plasma emission.

Changes in the neural network's plasma characterization output may indicate the end point of the plasma process and may be used to adjust a setting on the processing chamber. In an etch process, after the upper layer is etched through and the underlying layer is exposed the plasma reaction will change. The optical emission of the plasma also changes as the species of the plasma change. The spectrometer produces optical emission data representative of the optical emission and an algorithm or combination of algorithms is used to reduce the quantity of data. The reduced data is forwarded to the neural network. The trained neural network detects the change in plasma emission and changes the plasma characterization output to indicate the detection of the etch end point. The end point detection may be used to adjust the plasma processing chamber controls and/or indicate the plasma condition to an operator.

DETAILED DESCRIPTION

In the following description, for purposes of explanation, numerous specific details are set forth in order to provide a thorough understanding of the present invention. It will be evident, however, to one skilled in the art that the present invention may be practiced without the specific details. In other instances, well-known structures and devices are shown in block diagram form to facilitate explanation. The description of preferred embodiments is not intended to limit the scope of the claims appended hereto.

Figure 1:
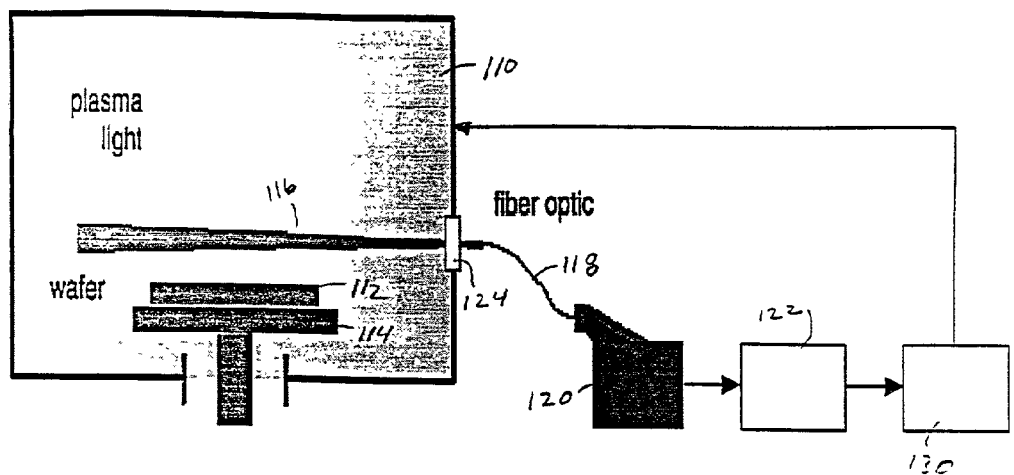
FIG. 1 is a diagram a plasma spectral analysis system.

The inventive system identifies plasma processes and indicates when plasma processing end points take place by analyzing the optical emissions from a plasma reacting with a substrate in a plasma processing chamber. The plasma processing chamber typically includes: a wafer chuck which holds a semiconductor substrate in the chamber during processing, an energy source and a process gas source. FIG. 1 is an exemplary hardware system used with the present invention. The wafer processing system includes at least one wafer 112 placed on a support 114 and exposed to a plasma. Light 116 generated by the plasma passes through a window 124 in the process chamber 110 and an optical fiber 118 to the spectrometer 120. The spectrometer 120 determines the intensity values for each optical wavelength emitted during plasma processing. The output data from the spectrometer 120 may be processed by an algorithm or combination of algorithms which reduce the quantity of optical emission data. Algorithms for reducing data include a peak finding algorithm and data reduction algorithms noise reduction algorithms and PCA algorithms. The reduced optical emission data is analyzed by a neural network 122 which identifies the plasma characteristics. The plasma characteristic output of the neural network may be forwarded to a system controller 130 which may adjust the process controls of the process chamber 110 and notify a system operator of the plasma characteristic when a plasma event is detected.

Figure 2:
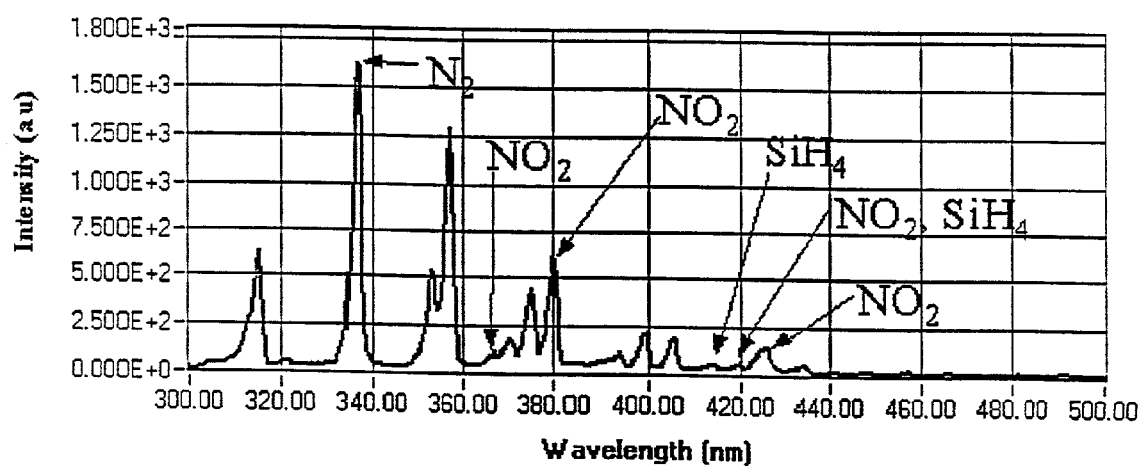
FIG. 2 is an exemplary plasma emission optical spectrum.

The optical emission data of the plasma can be analyzed by wavelength and amplitude to determine the specific species in the plasma. Chemical reactions takes place when the highly reactive plasma particles come into contact with the substrate resulting in the emission of specific wavelengths of light which indicate the specific species in the plasma reaction. FIG. 2 illustrates an exemplary optical wavelength spectrum output for an exemplary plasma emission. The X-axis is the optical wavelengths of the plasma emission from 300 to 500 nm and the Y-axis is the intensity of the emission ranging from 0 to 1,800 an. The entire optical spectrum produces a pattern of intensities at specific wavelengths which indicates all of the specific species in the plasma. In this exemplary optical spectrum, the presence of $N_2$, is indicated by the peak in intensity at 337 nm wavelength light. The presence of $NO_2$ is indicated by peaks of intensity at about 365 nm, 380 nm, 420 nm, and 425 nm. The presence of $SiH_4$ is indicated by the peaks at 415 nm and 420 nm wavelength light. For most plasma reactions the primary range of wavelengths of interest may be 300 nm to 750 nm. Monitoring wavelengths outside this range may be problematic because the optical signals tend to be noisy and difficult to measure accurately for some spectrometers. In alternative embodiments, spectrometers capable of monitoring wavelengths smaller than 300 nm and greater than 750 nm may be used in the same manner described above.

Table 1 is a listing of an example of a section of data produced by the spectrometer. For exemplary purposes the intensity is listed for every nanometer change in wavelength. The actual spectrometer may provide intensity data for every 0.1 nanometer change in wavelength.

TABLE 1

| wavelength (nm) | 332 | 333 | 334 | 335 | 336 | 337 | 338 | 339 | 340 | 341 |
|---|---|---|---|---|---|---|---|---|---|---|
| intensity (au) | 75 | 100 | 150 | 300 | 950 | 1,600 | 500 | 250 | 100 | 75 |

The wavelengths of light associated with each reaction may be constant for all plasma processes, but the amplitude of the emission depends upon the quantity of reactions. A low relative intensity indicates that few reactions are taking place and a high relative intensity indicates that many reactions are taking place. In an etch process, the amplitude of the optical emission may remain constant as the plasma reacts with a substantially constant surface area of an upper layer. At the end of the upper layer etch when the underlying layer of a different material is partially exposed, the surface area of the upper layer decreases and the amplitude of the optical emission may decrease because there is less material to react with. Eventually, the entire upper layer may be completely etched through and the only reactions may be with residual materials and the emission amplitude of the wavelengths associated with the upper layer etch may drop to nearly zero.

As the underlying layer begins to react with the plasma, the wavelengths of the emission change indicating a change in species in the plasma reactions. The change in emission wavelengths occurs because the species of the upper layer plasma reaction are different than the species of the lower layer plasma reaction. By detecting the changes in amplitude and intensity of the emission, plasma processing events can be detected. The immediate characterization of the optical emission can be used to change the processing conditions and improve substrate processing.

By monitoring the plasma emission the presence of specific molecules, ionic or species reactions in the plasma can be detected. If the spectral output remains constant, the plasma reactions and emissions taking place remain the same. Changes in the plasma emission may indicate a change in the plasma species and a plasma event. For example, if an etch plasma completely removes first layer of material and then begins to react with an underlying material, the spectral output will change indicating the presence of different molecules ions and species in the plasma. As discussed, the presence of specific molecules ions or species is indicated by specific wavelengths of light and changes in the plasma are indicated by changes in the intensity of specific wavelengths of light. By monitoring the spectral pattern (wavelengths and amplitudes) of the plasma and recognizing the molecular, ionic and species indicators, the inventive system can detect and/or predict plasma events.

Although the neural network of the present invention is capable of analyzing the full optical spectrum, this approach is problematic because there are thousands of distinct wavelengths which must be monitored. For example, if the spectrometer monitors all wavelengths between 300 nm and 550 nm at 0.1 nm increments, the total number of wavelengths monitored would be 2,500. Extremely high processing power is required to continuously monitor and analyze each of the 2,500 individual frequencies at a fast enough rate to detect and characterize the plasma emission in a timely manner.

If the optical emission data can be reduced the neural network is able to process information more quickly and the time of he plasma event detection is more accurate. In an embodiment, the inventive system includes an algorithm or combination of algorithms which significantly reduces the amount of data input into the neural network. The data reduction allows the neural network to operate faster because less information needs to be processed without compromising the accuracy of the plasma analysis.

The quantity of data inputs to the neural network may be reduced by processing the spectral emission data with a peak finding algorithm. The peak finding algorithm identifies the wavelengths of a plasma emission which are associated with specific species and filtering out all other wavelengths. As illustrated in FIG. 2, specific species are represented by peaks of intensity at specific wavelengths of light. The wavelengths associated with the specific species remain constant.

The "peak finding" algorithm defines peak wavelengths as the wavelengths between a rapid increase in intensity and a rapid decrease in intensity. The peak finding algorithm identifies the starting and ending wavelengths of each peak by scanning the wavelength axis, X-axis of the spectral plasma emission of FIG. 2. The leading edge of a peak is defined as the wavelength at which the intensity exceeds a specified rate of rise immediately after a relatively small change in intensity. Similarly, the trailing edge of a peak may be defined as the wavelength at which the intensity exceeds a specific rate of decline followed by a relatively small change in intensity. More specifically, the beginning or ending wavelengths of a peak may be defined as the wavelengths at which the change in intensity per change in wavelength ($\Delta$ intensity/$\Delta\lambda$) exceeds a specific value.

For example with reference to Table 1, the rate of rise for a leading edge of a peak may be 50 au/nm. At 332 nm, the change in intensity/wavelength=(100−75 au)/(333−332)=25 au/nm which may be a relatively small change in intensity.

At 333 nm the rate of rise is (150−100 au)/(334−333 nm)=50 au/nm which satisfies the algorithm requirement for the leading edge of a peak. In this example the leading edge of the peak is detected at 333 nm wavelength. Using a similar calculation, the trailing edge of the peak is at 340 nm wavelength. After the peak finding algorithm identifies the wavelengths associated with spectral peaks, it transmits the reduced emission information associated with the species of the plasma to the neural network. Wavelengths not associated with the peaks can be filtered from the optical emission data, reducing the quantity of data transmitted to the neural network.

To further reduce the quantity of data analyzed by the neural network, the inventive system may also include a "data reduction" algorithm. The data reduction algorithm solves a single value representing the cumulative intensities for all wavelengths in each plasma emission peak. The quantity of data is reduced because the neural network only has to analyze a single intensity value for each peak rather than the intensity values for each wavelength of the peak. The data reduction algorithm solves the cumulative intensity for each peak as the "area" under the peak which is a function of the wavelength range and the cumulative emission intensity. For example the presence of $N_2$ in a plasma may be detected by determining the area under a frequency band from 333–340 nm. The area of the peak may be equal to the sum of the intensities for each wavelength of the peak. The sum of the intensities for each wavelength=$\Sigma(\Delta\lambda)(I)$, where $\Delta\lambda$ is the difference in wavelength between intensity measurements and I is the measured intensity.

In a simplified example using the data from Table 1, the intensities of the wavelengths for the $N_2$ may be as listed in Table 1 below. The difference be wavelengths is 1 nm, thus $\Delta\lambda$=1 nm. The $\Sigma(\Delta\lambda)(I)$=3,850 nm au based upon the sum of intensity values of Table 1 and represents the cumulative intensity of the 337 nm wavelength peak. By solving a single value for the emission areas of each peak, the data analyzed by the neural network can be reduced significantly without reducing the accuracy of the plasma event detection.

The quantity of data points for all measurable plasma emission frequencies may be about 2,500 while the same plasma emission processed to determine the "areas" under the peaks may be about 103 data points. The peak finding algorithm significantly reduces the number of data points and required processing power while preserving the accuracy of the spectral information. The required neural network processing power may be proportional to the number of inputs. By reducing the inputs from 2,500 to 103 input signals will drastically reduce the required processing power without compromising the accuracy of the plasma event detection.

An alternative means of reducing the emission data transmitted to the neural network is by processing the data with a "noise reduction" algorithm which removes/filters low level noise signals from plasma emission signal. The filtration of noise improves performance of the system by removing signals unrelated to plasma emissions by allowing only relevant data signals to be processed by the neural network. The noise reduction algorithm may define noise as any signal that is less than a minimum spectral width (wavelength range) and any signal that is less than a minimum noise level intensity. In an embodiment, the noise reduction algorithm classifies any signals having a frequency range of less than about 3 nm or an intensity of less than about 50 au as noise that may be filtered from the signal. The noise data is filtered out of the spectral intensity data which is forwarded to the neural network.

Principal component analysis (PCA) is another method for reducing data by extracting information by finding direction in input space in which the inputs exhibit the most variation. PCA is a well known mathematical procedure that transforms a number of possibly correlated variables into a smaller number of uncorrelated variables called principal components. The first principal component accounts for as much of the variability in the data as possible, and each succeeding component accounts for as much of the remaining variability as possible. Principal component analysis is accomplished by centering the data by subtracting the mean value in each dimension. Traditionally, principal component analysis is performed on a square symmetric matrix. By applying PCA to the spectral emission data from the spectrometer, the number of data points can be reduced.

Figure 3:
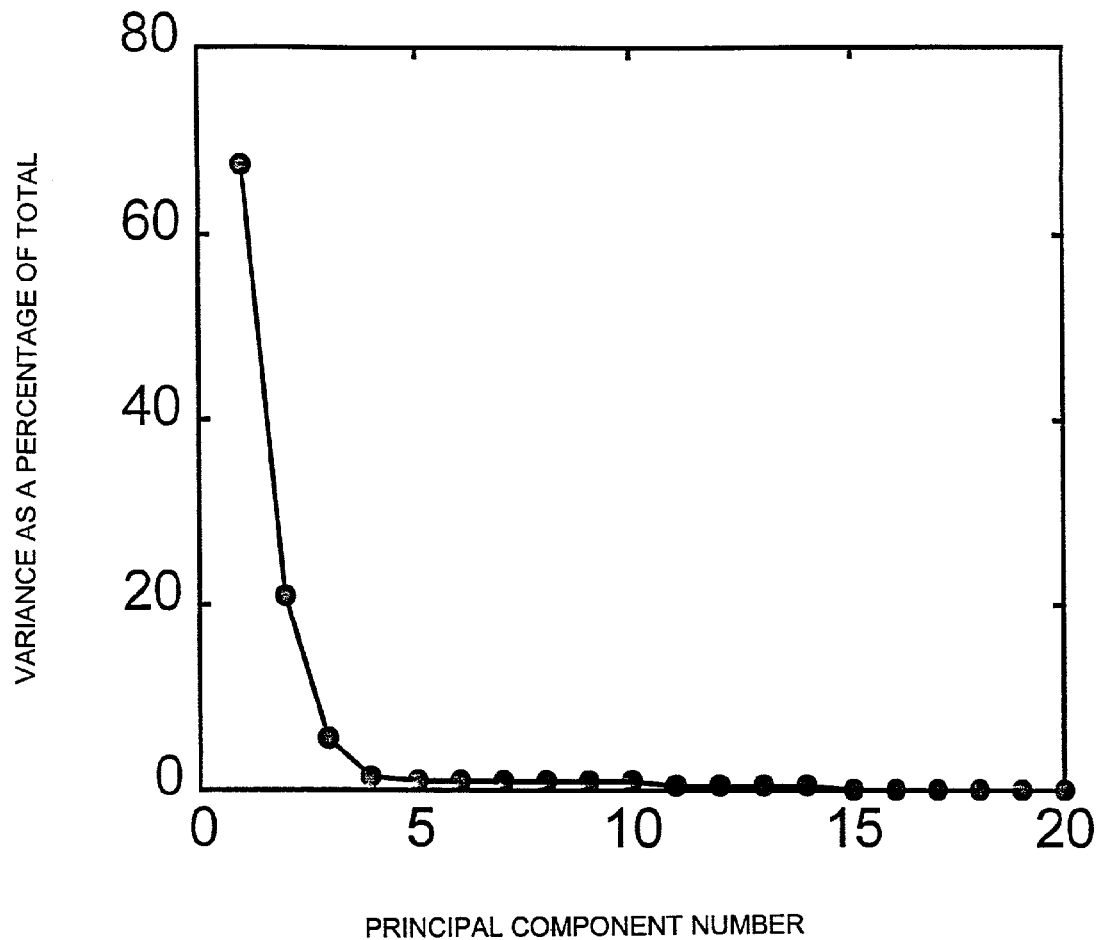
FIG. 3 is chart showing variance as a percentage of total based upon the number of principal components processed.

As discussed, by using the data reduction algorithm, the optical spectrum of a plasma is reduced to 103 input signals representing the area (intensity) under the peak signals. FIG. 3 is a plot of the percent variance contribution of each principal component (PC) according to the present invention for a PCA performed on the 103. Only the first 20 out of 103 principal component inputs are shown on the X-axis. In this example, the variance as a percentage of total dramatically decreases and quickly drops to a very low value which is close to 0. The variance as a percent of total continuously falls to a level of about $1 \times 10^{-2}$ by the $20^{th}$ principal component. The remaining principal components have a similar low level of about $1 \times 10^{-2}$. Thus, only the first few principal components contain the characterization information which is processed by the neural network. By processing the plasma emission data with a PCA algorithm, the quantity of input data may be significantly reduced.

Several algorithms have been described to reduce the quantity of data transmitted to the neural network including: peak finding, noise reduction, data reduction and principal component analysis. Although these algorithms have been described as being used in combination, they are not mutually exclusive. The algorithms may be used independently or in any combination to reduce the quantity of data transmitted to the neural network. Further, the present invention may also be compatible with other types of data reduction algorithms not described above which may be used independently or in combination with any of the described algorithms.

The neural network characterizes the plasma based upon an analysis of the optical emission data. Various types of neural networks are compatible with the inventive system. Broadly defined a neural network may be a computer architecture in which a number of processors are interconnected in a manner suggestive of the connections between neurons in a human brain and which is trained using a learning process. In principle, neural networks can compute all functions except for those having an infinite number of discontinuities. Neural networks are particularly useful for classification and function approximation and mapping problems where there is a tolerance of some imprecision.

Figure 4:
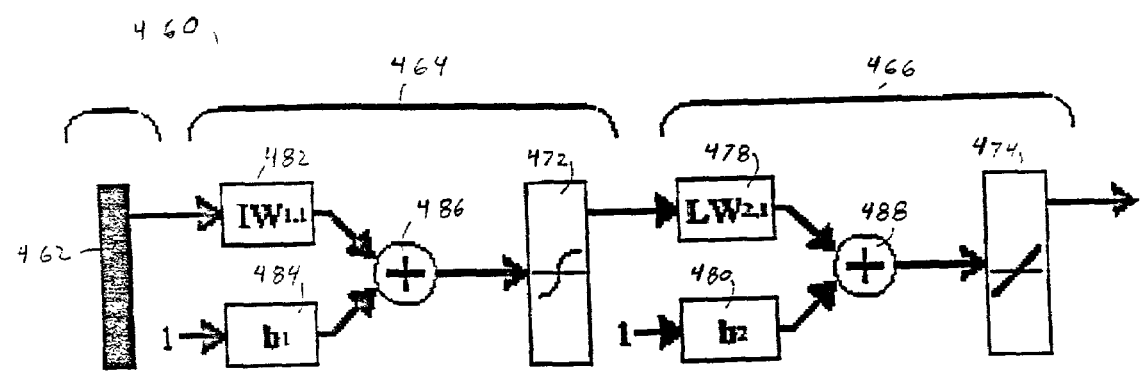
FIG. 4 is a diagram of a two layer neural network.

FIG. 4 is a diagram of the architecture of a multi-layer neural network 460. For illustrative purposes only a single input and neuron are shown per layer. The illustrated neural network 460 includes a first layer 464 and a second layer 466. A basic layer includes a plurality inputs, neurons and a transfer function. A spectral input signal 462 representing a portion of the plasma emission is transmitted to the neuron in the first layer 464. The first layer neuron processes the input signal (I) 462 by multiplying it by an associated weight ($W_1$) 482 and adding a bias ($B_1$) 484 to the multiplied signal at the sum 486 so that the neuron output signal becomes $IW_1+B_1$. The weighted and biased signal is fed to a first transfer function 472. In an embodiment, the transfer function of the first layer is a sigmoid transfer function. The output of the first layer transfer function 472 is transmitted to a neuron in the second layer 466. The second layer neuron multiplies the signal (L) with a weight ($W_2$) 478 and then adds a bias ($B_2$) 480 at the sum 488 so that the second layer neuron output signal becomes $LW_2+B_2$. The second layer neuron output is fed to a second layer transfer function 474. In an embodiment, the second layer transfer function is a linear transfer function. The output of the second transfer function is the neural network's characterization of the input data.

The neural network illustrated in FIG. 4 only represents a single input system and is only used to illustrate the basic operation. The actual neural network used has multiple inputs and neurons for each of the inputs. As discussed, by processing the emission data reduction algorithms the neural network may have fewer than 103 inputs, each of which is fed to a first layer neuron and processed in the manner described above. The outputs of the first transfer functions are then be fed to inputs of the second layer. A neural network may be infinitely expandable by adding additional layers and inputs. Because individual neurons may be required for each input signal, a plasma characterization system monitoring all wavelengths of the optical spectrum (2,500 inputs) will require an extremely large neural network. By reducing the quantity of inputs to less than 103, the neural network can be much smaller and can process the input information faster.

There are many types of neural networks which are categorized by processing characteristics. There are two main types of networks, feedforward and feedback. In a feedforward neural network, the connections between units do not form cycles. Feedforward neural networks usually produce a response to an input immediately because the neural does not cycle signals. In a feedback or recurrent neural network, there are cycles in the neuron connections resulting in a slower response. In some feedback neural networks, each time an input is presented, the neural network must iterate for a potentially long time before it produces a response. The operating characteristics and learning systems which have a fast processing speed are generally compatible with the inventive system.

Neural networks are extremely powerful and flexible in their processing capabilities because they are capable of being trained to process information in the desired manner.

Specifically, the weights and biases of the neurons of the neural network may require adjustment to produce the desired output. The weights and biases of the neural network are adjusted during a training procedure. There are several methods for training a neural network. The two main types of training algorithms are supervised and unsupervised. In supervised training, the correct results (target values and desired outputs) are known and are given to the neural network during training so that the neural network can adjust its weights to try to match the outputs to the target values. The manual training of the neural network require a large set of various plasma emission training data with the values adjusted or validated by human experts. The weights and biases may continue to be adjusted even after the neural network is used in production. In an alternative embodiment, after the neural network is trained to produce the target results, the weights and biases may be set and the neural network may be used for the trained application without further adjustments.

For purposes of explanation herein, the manual training of the neural network will be described with respect to a plasma etch process. In this example, the plasma etches through 3 layers of a wafer, thus 4 separate layers are exposed to the plasma each having a different plasma emission. During etching a specific plasma emission is produced for each layer. When the layer is etched through, the underlying layer is exposed and the plasma emission changes. The spectrometer is exposed to the plasma emission and transmits data representing the plasma emission to the neural network which characterizes the plasma. During the plasma etch process, the exposed layer is removed which exposes an underlying layer which is then etched. As the etch transitions from the upper to the lower layer, the plasma emission changes. The transition from etching an upper layer to the underlying layer is known as a "plasma event." Because the plasma etches through 3 layers, the neural network must categorize 4 different plasma emissions and detects 3 plasma events. The detection of the third plasma event is used as the end point detection for the etch process. The neural network must determine the precise time of the plasma events to provide useful endpoint detection information.

The training data includes plasma emission, plasma characterization and event timing data for the entire etch process is provided to the neural network. The plasma emission data is processed by the neural network and the output of the neural network is compared to the correct plasma characterization. In this example the plasma process requires about 300 seconds and training data is provided for each second of the process. The emission data for each second is fed to the neural network which outputs characterization information. After all emission data is processed the neural network outputs are compared to the correct plasma characterization. Based upon the errors between the output of the neural network and the correct plasma characterization, the weights and biases of the neural network are adjusted. After the weights and biases are adjusted, the plasma emission data is again processed by the neural network, which produces results closer to the correct characterization. Each run through a set of emission data is known as an epoch. As the process continues the errors between the neural network and the output become smaller until there is no significant improvement in results.

In this example, the known processing data for 8 wafers is used to train the neural network to characterize the plasma etch process. The "plasma event" data for the 8 wafers is listed in Table 2. Event 1 indicates the time in seconds for completion of the first layer etch. Similarly, Event 2 and Event 3 indicate the completion of etching the second and third layers, respectively. Because there are four plasma characteristics, the output of the neural network may be 0, 1, 2, or 3, which is the characterization of the optical emissions of the plasma during the first layer etch, second layer etch, third layer etch and forth layer etch, respectively. The specific plasma emission data for each wafer is not listed in Table 2, however the correct characterization of the plasma corresponds with the event times. For example, for wafer 1 the plasma characterization is 0 for time=0 to 26.58 sec., 1 for 26.58<time<67.56, 2 for 67.56<time<215.03 and 3 for time>215.03.

TABLE 2

|  | Event 1 | Event 2 | Event 3 |
| --- | --- | --- | --- |
| Wafer 1 | 26.58 | 67.56 | 215.03 |
| Wafer 2 | 29.71 | 46.08 | 208.88 |
| Wafer 3 | 28.67 | 45.09 | 207.89 |
| Wafer 4 | 28.67 | 37.90 | 204.82 |
| Wafer 5 | 27.63 | 34.82 | 205.80 |
| Wafer 6 | 27.63 | 35.81 | 205.80 |
| Wafer 7 | 25.65 | 33.83 | 204.82 |
| Wafer 8 | 26.59 | 34.77 | 206.85 |

The data set in table 1 for the 8 wafers may be divided into a training, validation, and test sets in a 25/25/50% distribution, i.e. 2 wafers training, 2 wafers validation and 4 wafers test. The training of the neural network as described above is performed with the data from both wafer 1 and wafer 2 data sets. If the training process and adjustments to the weights and biases continues through too many epochs, the weights of the neurons may be "overfit" resulting in an increase in errors. In order to prevent overfitting, the wafer 3 and wafer 4 validation data is used to check the improvement of the weight settings of the neural network. During the training with the validation data is periodically run on the neural network with the weights and biases not yet in final settings. As discussed, the error initially typically gets smaller and normally the results improve. If the validation neural network outputs of the set begin to get worse rather than better, training (adjustments of the weights and biases) may be stopped to prevent overfitting. The test data for wafers 5–8 is only used to check the results of the neural network with adjusted weights and biases.

The neural network is run on the data set associated with table 2. As discussed, the data is run on the neural network and the outputs are compared to the known data. The difference between the neural network output and the known plasma characterization is the error. In an embodiment, the output of the neural network may be a decimal value between integers while the known plasma characterizations are the integers 0, 1, 2 or 3. Thus, the difference between the neural network output and the correct characterization may be a decimal.

Figure 5:
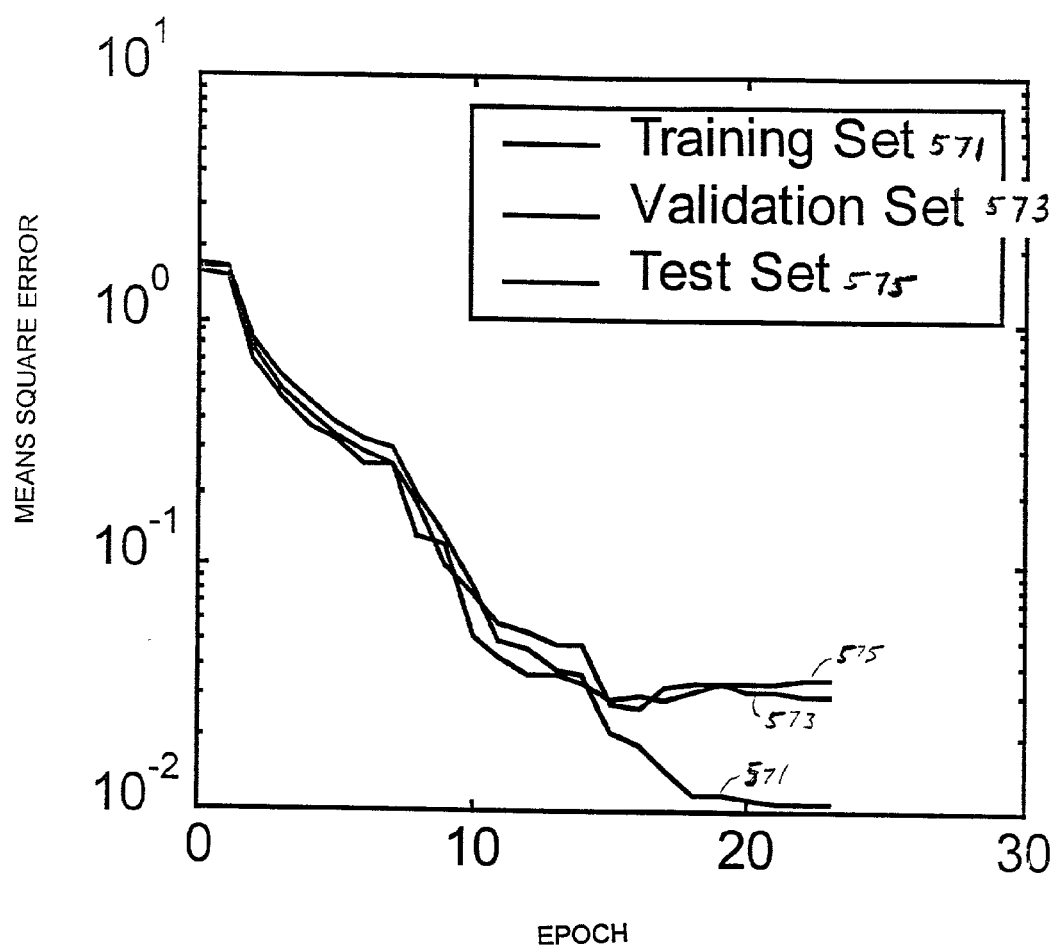
FIG. 5 is an exemplary plot of the mean square error under supervised learning in a feed-forward neural network.

FIG. 5 is a plot of the mean square error in classification output of the neural network for a wafer under supervised learning in a feed-forward neural network. Each iteration through a set of training data is known as an epoch. The mean square error is indicative of the output of the neural network based upon the number of epochs used to train the weights and biases of the neural network. The mean square error is used as the performance measurement that is representative of the number of input vectors that were correctly classified. In this example, data from wafer 2 was divided into training, validation and test sets. The neural network is normally trained using the training data, but any known data may be used.

The errors in the output of the neural network are tracked as the weights and biases were adjusted during training. The training set 571 may be used to alter the weights and biases, then the neural network may be used with the validation set 573 and test set 575. The error is at first high and then decreases significantly until it is about $3 \times 10^{-2}$ by the $13^{th}$ epoch. The error in the training set 571 begins to rise slightly at the $19^{th}$ epoch and at the $17^{th}$ epoch for the validation set 573 and test set 575. As discussed, this increase in error is an indication of overfitting. When overfitting is detected by an error increase the neural network settings against the validation set 573, the training and adjustments to the weights and biases may be stopped. While the validation set is not used update the weights and biases, it is used to detect overfitting and the point at which the training should be stopped. The test set is only used to check of the performance of the neural network.

Figure 6:
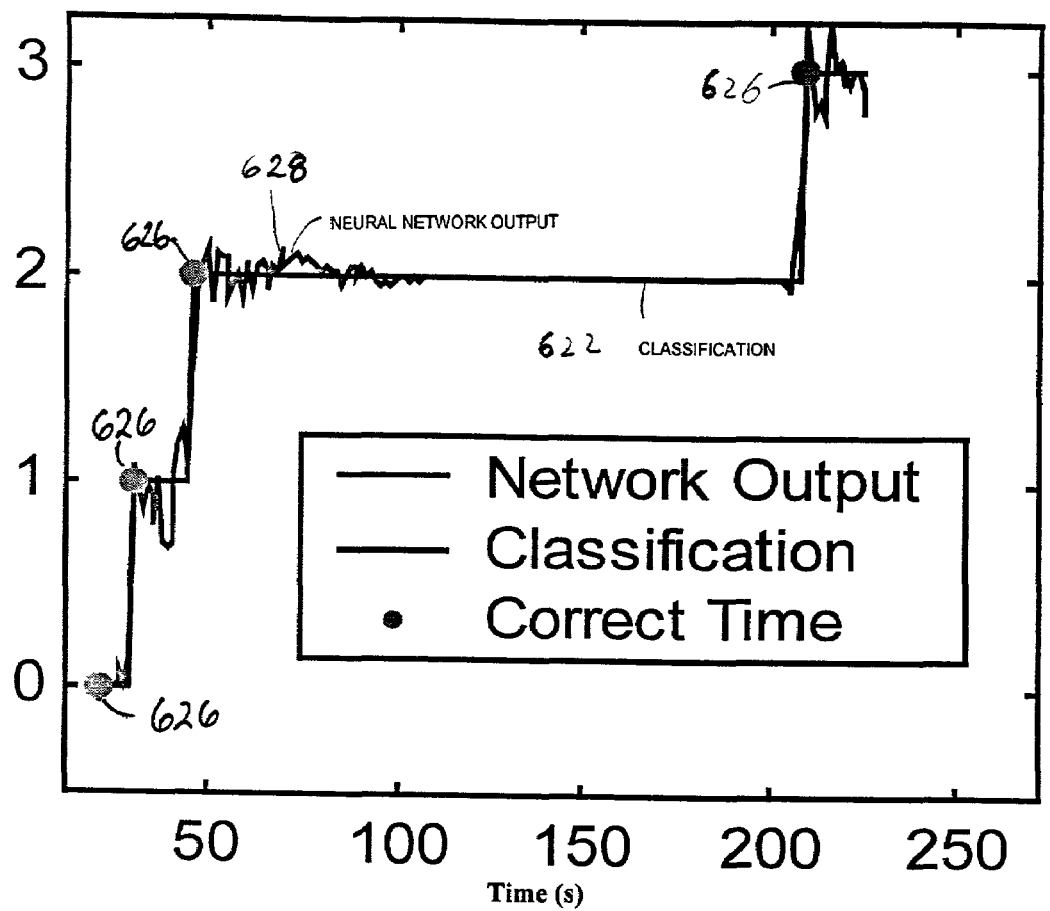
FIG. 6 is an exemplary plot of classification results from the inventive system.

Although correct classification of the spectral output is important, the detected time of the changes in classification (plasma events) is used to detect the processing end point and is more important. FIG. 6 is a plot of the input vector classification 622 as a function of time for reduced data representing the spectral emission processed by a trained neural network. As discussed, the output of the neural network is one of four classifications 0, 1, 2 or 3 (equally spaced on the vertical axis). The network output 628 is the raw decimal value returned by the neural network. Thus, the network output 628 does not always lie directly on 0, 1, 2 or 3. In the actual plasma characterization system, the classification 622 is the network output 628 rounded to the nearest integer 0, 1, 2 or 3. The transition times of the classifications which are vertical movements of the classifications indicate the plasma events. The known correct transition times for plasma events is represented by circles 626. For this exemplary set of data, the circles 626 are located on the leading point of the changes in neural network output 628 and plasma classification 622, indicating a very close correlation between the predicted time of the plasma events and the known correct time of the plasma events.

Unsupervised training does not require training data to be input into the neural network. The neural network may include a self organized or self adjusting system which automatically sets the weights and biases of the neural network in an iterative process using any plasma emission data. The neural network automatically determines clusters in the data set. The data points lying close together are then put into one category. The number of categories (clusters) that are found depends on the structure of the neural network. In unsupervised training only the general categories for all data points is specified, the neural network then automatically puts the data points close together in each of the categories. In contrast, supervised training requires that the category of each data point be specified.

More specifically, plasma emission data may be input into the neural network which then processes data using arbitrary weights and biases. The characterization outputs of the neural network are then compared to each other. Before the weights and biases are fully adjusted, the outputs from the neural networks will fall into multiple clusters. The weights and biases of the neural network neurons are then automatically adjusted to reduce the differences between the outputs in each cluster. The neural network adjustment process may be repeated until the neural network output correctly characterizes plasma emission or alternatively the weights and biases may continue to be adjustable even during normal production processing.

Figure 7:
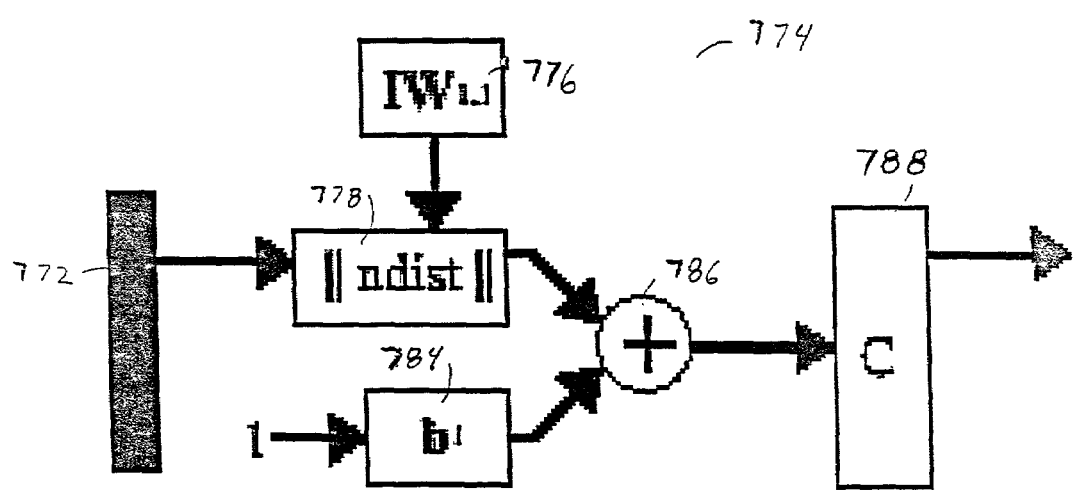
FIG. 7 is a diagram of a competitive neural network layer.

In an unsupervised training embodiment, a "competitive" neural network may be used. Competitive neural networks are self organized and allow the neurons to associate themselves with specific input vectors. FIG. 7 is a diagram of the architecture of the competitive neural network. The input is a single vector 772 which comprises R elements. The weight matrix IW 776 contains a weight vector for each of the neurons in the competitive layer 774. Both the single vector 772 and the weight matrix IW 776 are processed by the ndist function 778 which calculates the distances from the weight vectors to the input vector 772. Thus, for each neuron of the neural network, the distance from that neuron to the input vector is calculated. The output of the ndist function 778 and the bias 784 are added at the sum 786 and fed to the competitive transfer function 788. The output of the competitive transfer function 788 is 1 for the neuron having the smallest distance (the winning neuron) and a 0 for the remaining neurons. The distance between clusters is indicative of how dense that particular region is. Thus, not only are the different regions indicated, but also the relationship between the regions.

Figure 8:
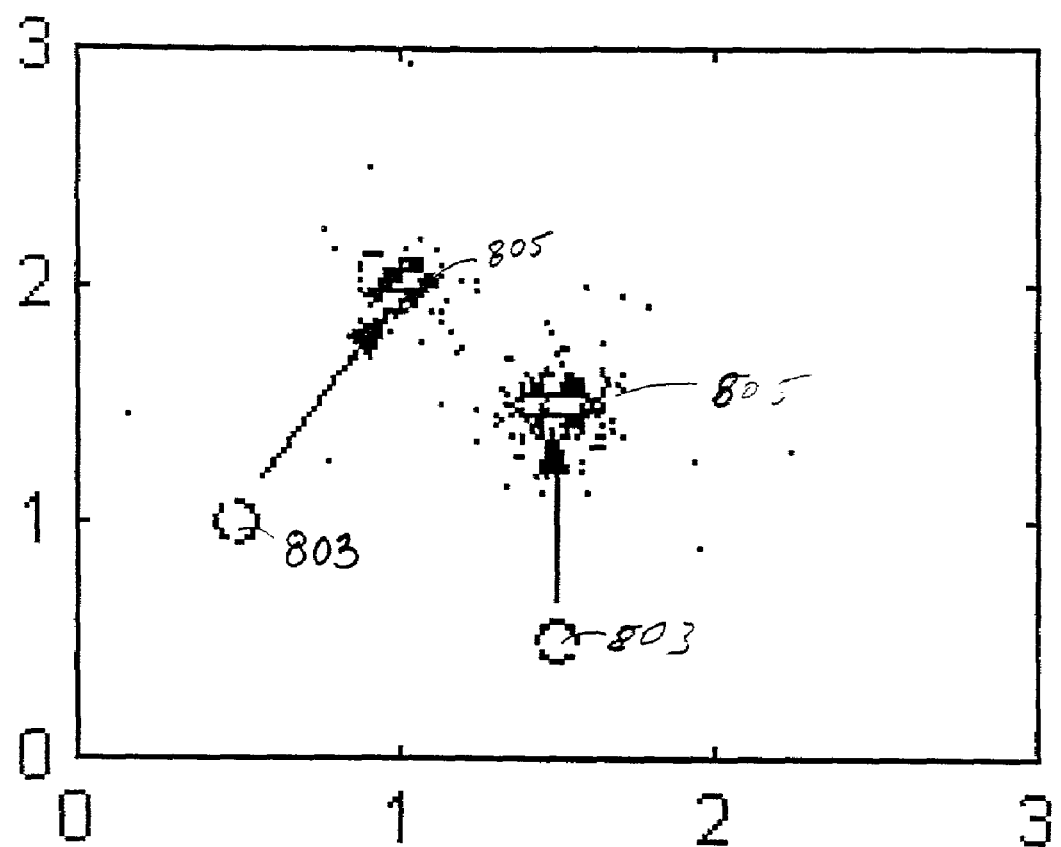
FIG. 8 is an exemplary plot of automatic clustering with a competitive neural network.

With reference to FIG. 8, a graphical representation of the neuron weights 803 and clusters of input vectors 805. This unsupervised learning rule therefore causes the neuron's weights 803 to produce neural network outputs which are adjusted during training to approach the centers of the clusters of input vectors 805. When other similar input vectors are considered, the same neuron will again have the smallest distance and its weight 803 is adjusted to approach each of the similar input vectors 805. The end result of the Kohonen learning rule is that the neuron weight will be centered between all those input vectors to which it was the closest. Similarly, other neurons weights will be positioned near other input vectors.

The Kohonen Learning technique may be used to adjust the weights of the winning neuron the weights of the other neurons remain unchanged in a competitive neural network. Referring back to FIG. 7, before training begins, the weight matrix IW 776 is given an arbitrary value. The weight of the winning neuron is modified by adding a correction factor.

The correction factor is the difference between the input element and the corresponding weight multiplied by the learning rate. This value is added to the weight value from the previous iteration. Eventually, the weights and biases of the neural network are adjusted to provide a generalized characterization of the plasma emission.

A potential problem with the Kohonen learning rule is that a first neuron which is initially far from both clusters will never have its weights adjusted to approach the cluster. This is because a second neuron that is closer to both clusters will always "win" the competition for input vectors in either cluster. This will cause the second neuron to become centered between the two clusters while the position of the first neuron will not change. To avoid this result, the well-known technique of conscience learning can be used. In conscience learning, the "winning" second neuron can be made "sympathetic" to the "losing" first neuron. This is accomplished by increasing the distance value for neurons that keep losing relative to those that keep winning. Eventually, the losing neuron will win and thus begin having its weights adjusted.

A further extension of the competitive neural network cluster analysis are self-organizing feature maps ("SOFM"). A SOFM can also provide information on the topography of the various clusters. The architecture of a network for SOFMs is similar to the competitive neural network architecture of FIG. 7 but does not include the biases. A difference between a competitive neural network and a SOFM can be the learning rule employed. In a competitive neural network, only the weights of the winning neuron are updated. By contrast, in an SOFM, the winning neuron and neighboring neurons all have their weights updated, albeit with a smaller learning rate. This difference can significantly affect the final weights of the neurons.

A self organized feature map utilizes a "self organized neural network" in which all neurons are arranged alongside one another in an "input space." The input space is a n-dimensional vector space in which the input data can be plotted over time as a trajectory path through the input space, where n is the total number of inputs. The spatial location of the individual neurons and the sequential relationship with other neurons in the input space distinguishes self organized neural networks from conventional neural networks.

As discussed, by processing the input data with a PCA algorithm, the spectral data is converted to principal components (PCs) and the first PCs represent the largest variations in data. The trajectory paths of the PCs (principal components) over time of the self organized feature map and the density of data points in each region thereof can also be used to characterize the PCs of the plasma emission. In the SOFM, data from process events can be discrete process trajectories rather than being subdivided into various data clusters. The value of the PCs can be plotted in the n-dimensional input space to determine trajectory paths of the PCs over time. Systematic patterns in the trajectory paths can indicate plasma processing events. The times associated with the plasma events can be determined by identifying the point at which the trajectory pattern changes.

Figure 9:
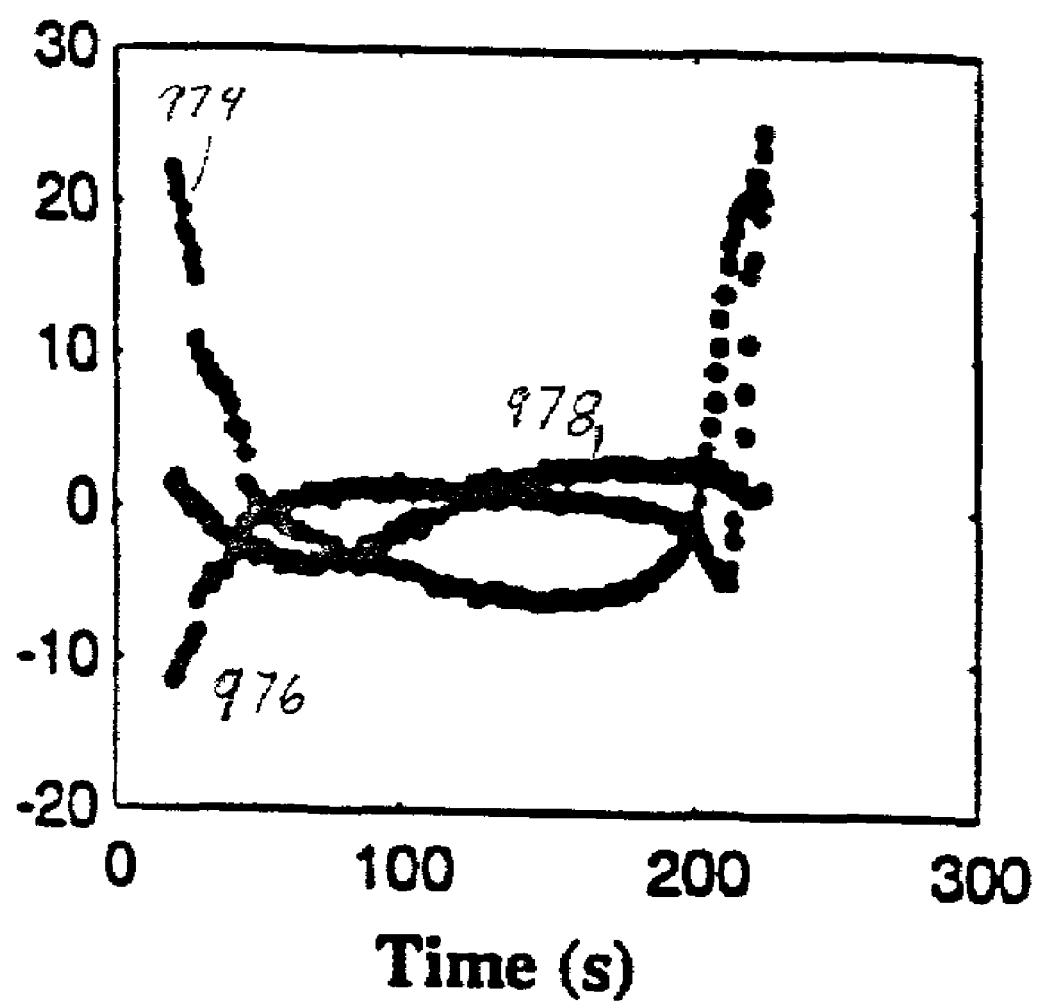
FIG. 9 is a plot of three exemplary principal component values v. time for a neural network.

FIG. 9 illustrates the values of three principal components: PC1 974, PC2 976, and PC3 978 for the exemplary wafer process discussed with reference to Table 2. The PC data is plotted on the Y-axis and the X axis represents the processing time. Data was taken at one second intervals, i.e. a rate of 1 Hz, however in practice any sample rate may be used. In this example each point represents the PC value at a specific second of processing. The gaps between adjacent points of a PC indicate the quantity of change in the PC values. Where there is a small gap between points, there is a small change in the PC value and conversely if there is a large gap there is a large change in PC value. The illustration of only three PCs in a three dimensional space for clarity. In practice, the inventive system will normally monitor many more PCs.

Figure 10:
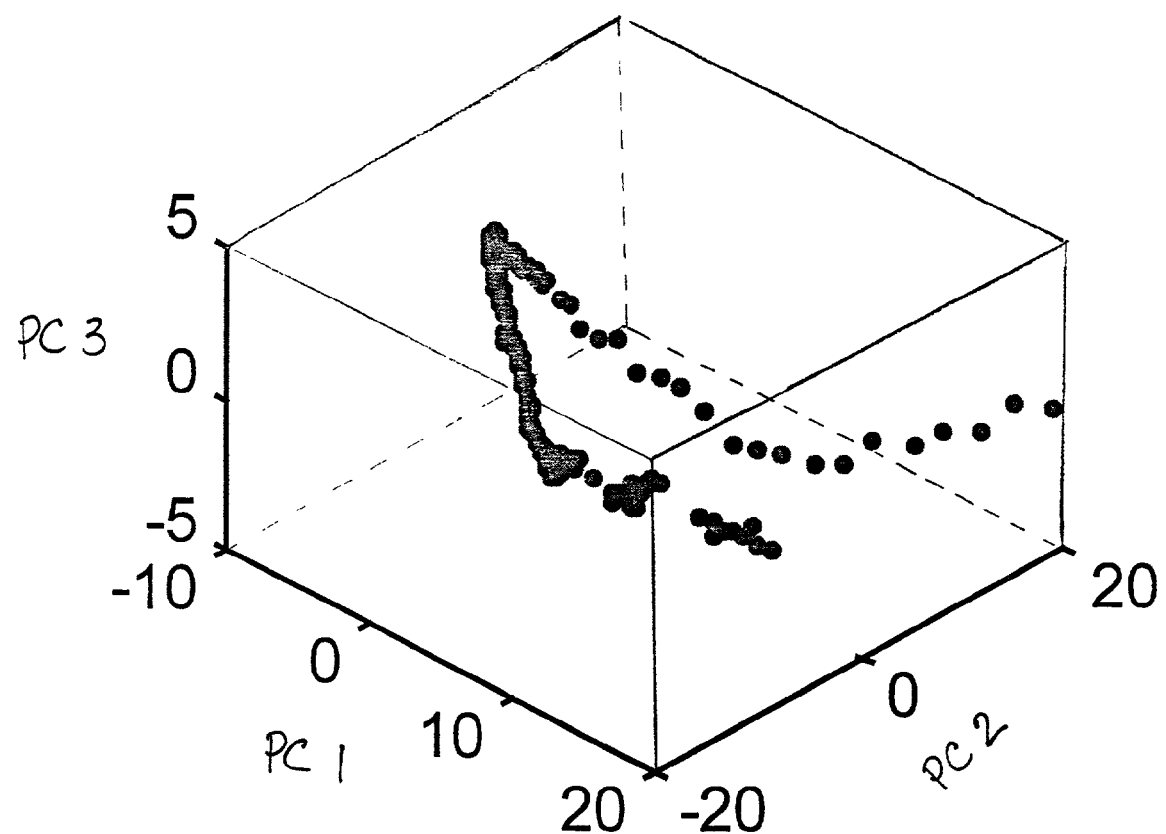
FIG. 10 is a three dimensional plot of three exemplary principal component values.
Figure 11:
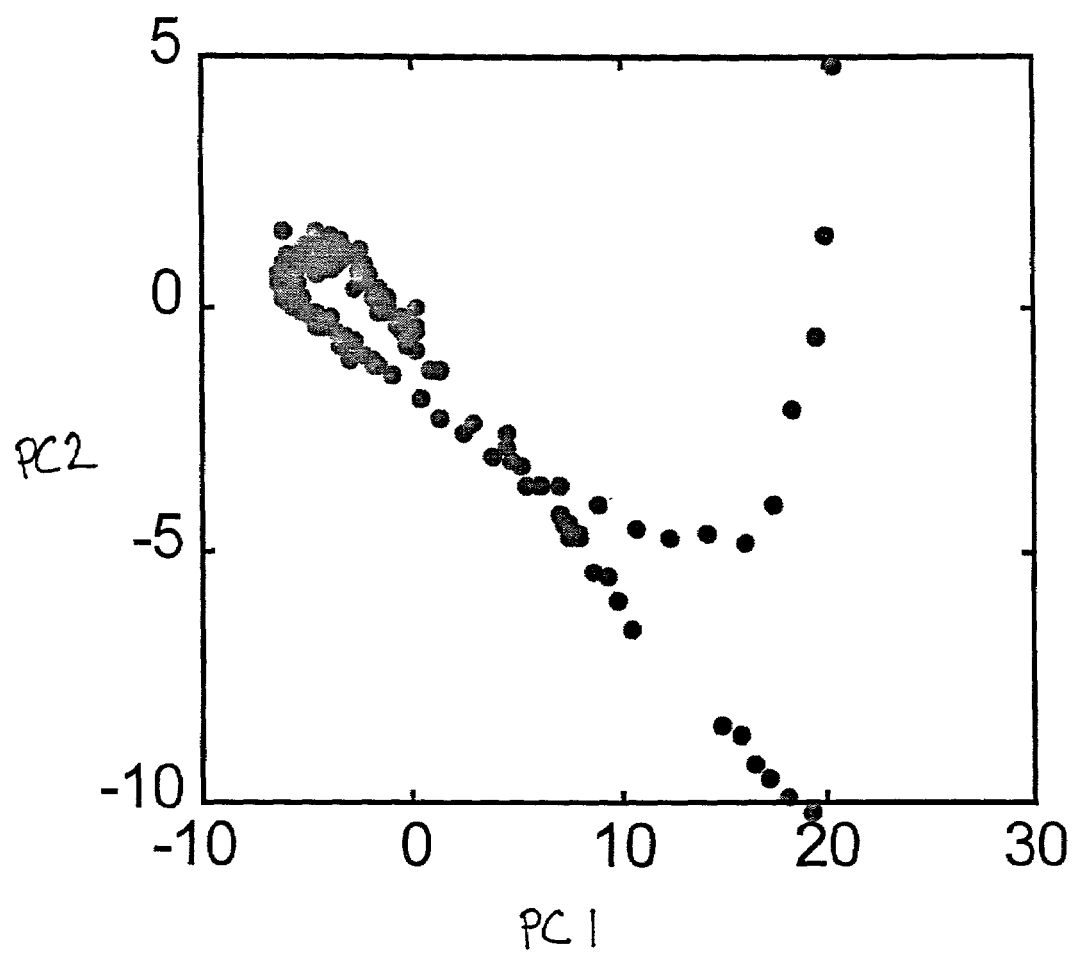
FIG. 11 is a two dimensional plot of the trajectory of two exemplary principal components values.

FIG. 10 is a three dimensional graph of the input data from FIG. 9 in the input space. Each of the three PCs represent a different axis of the three dimensional plot. PC1 is represented by the X-axis, PC2 is represented by the Y-axis and PC3 is represented by the Z-axis. Each point indicates a specific time and the coordinates of each point represent the corresponding values of PC1, PC2 and PC3. By plotting the three PCs over time a three dimensional trajectory representing the plasma emission evolves. Curves in the trajectory pattern indicate changes in plasma emission. Determining the derivatives of these curves is a potential way to determine when major changes in the plasma emission occur. However the derivative method may problematic because the results may contain erratic results. In order to improve the results a smoothing algorithm may be used to smooth out the erratic output.

Figure 12:
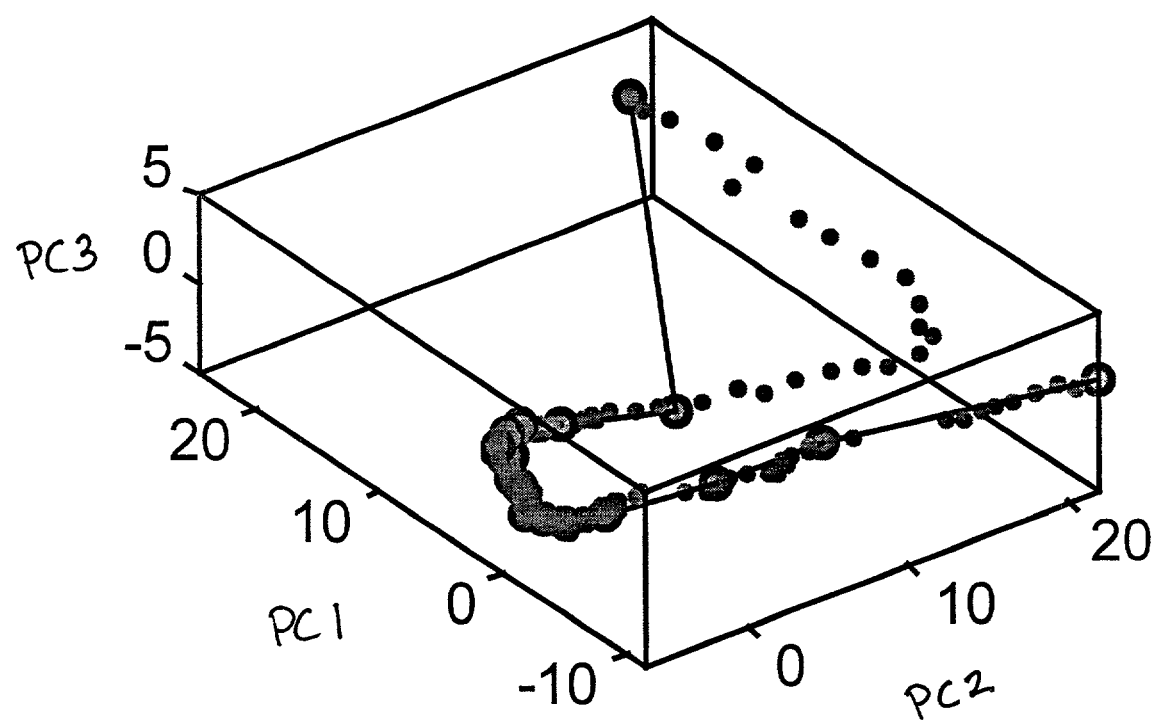
FIG. 12 is an exemplary self-organizing feature map according to the present invention.

In an embodiment, a SOFM having 18 nodes is trained on data from Wafer 2 as listed in table 2. In the FIG. 12, Each point plotted on the three dimensional graph is representative of the value of PC1, PC2 and PC3 at even time intervals. The SOFM is initialized such that the neurons are positioned on the PC's trajectory. In addition, adjacent neurons are placed adjacent to one another on the trajectory. The beginning and ending neurons are not considered part of the map and have been manually added. The weights of the start and finish neurons are set to be equal to the training data vectors to manually position the start and finish neurons. Significant changes in direction and spacing between plot points may indicate plasma characterization changes.

Figure 13:
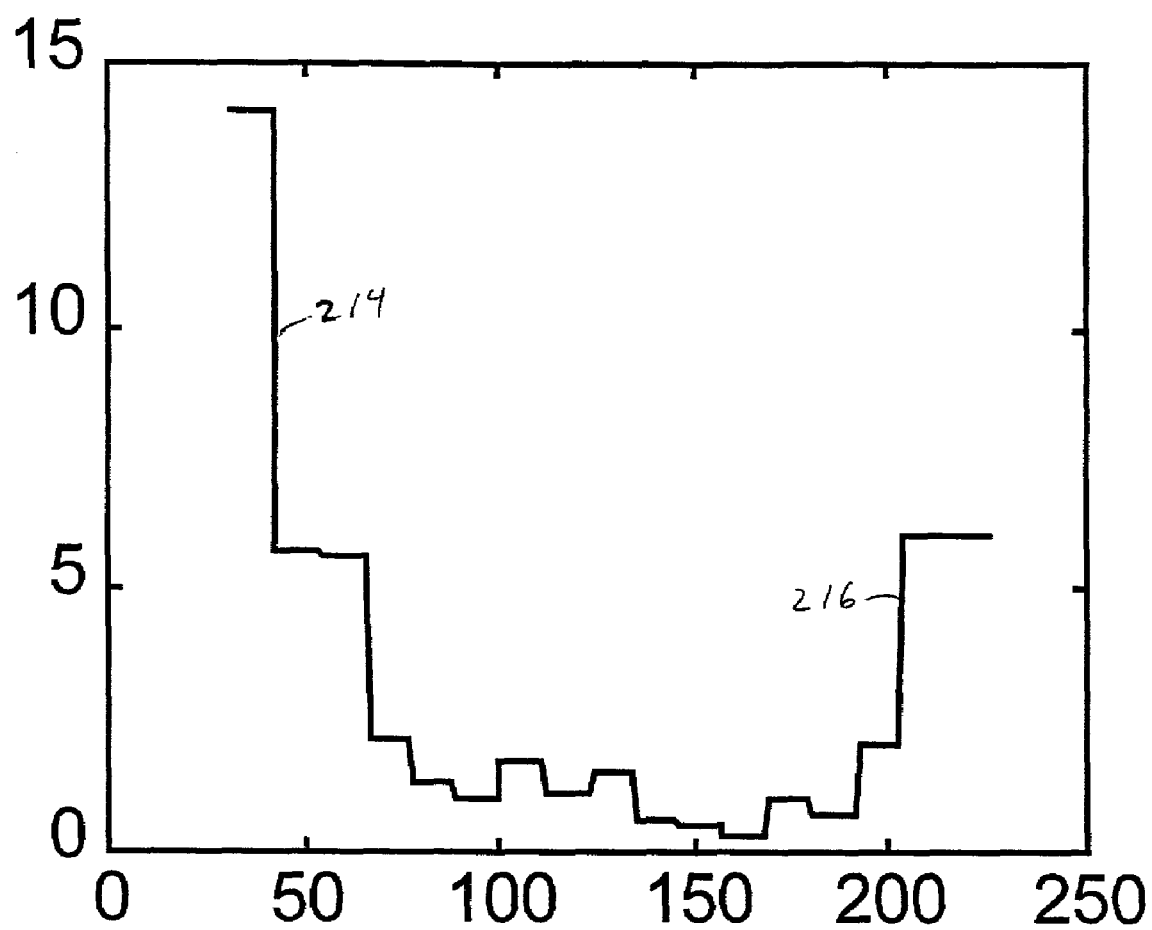
FIG. 13 is a chart illustrating the magnitude of change of the exemplary plasma emission during the wafer processing time.

FIG. 13 is a two dimensional graph illustrating the variations in plasma emission during plasma processing. The vertical axis represents the distance between adjacent neurons illustrated in FIG. 12. Large variations or jumps in vertical axis plots may indicate plasma characterization changes. For example, a first jump 214 from about 14.3 to 5.6 and a second jump 216 from about 2.1 to about 5.1 shown in FIG. 13 occur at times equal to 43.01 and 203.77 seconds, respectively. These event times are similar to the targets of Table 1, in which the plasma event times were listed as 46.08 and 208.88 seconds, respectively. Using the SOFM according to the present invention provides additional information that can be used to detect other events and to provide a more detailed analysis of the process chemistry.

The present invention describes a system in which the quantity of optical emission data is substantially reduced before being processed by a neural network to improve the processing speed of the system. Because the data reduction processes used do not remove critical optical emission information, the inventive system is also able to produce highly accurate plasma characterization results.

Although the present invention has been described with reference to specific exemplary embodiments, it will be evident that various modifications and changes may be made to these embodiments without departing from the broader spirit and scope of the invention as set forth in the claims. Accordingly, the specification and drawings are to be regarded in an illustrative rather than a restrictive sense.

What is claimed is:

1. A plasma processing system, comprising:
    a plasma processing chamber capable of processing a substrate with a plasma;
    a spectrometer for monitoring an optical emission of the plasma and producing a optical emission data;
    an algorithm for reducing the quantity of optical emission data by adding the optical intensities for a range of wavelengths to determine a single cumulative optical intensity representing the cumulative emissions of a range of optical wavelengths associated with a single plasma emission peak; and
    a neural network for detecting a plasma processing event by analyzing the reduced optical emission data.

2. The plasma processing system of claim 1, wherein the algorithm is a peak finding algorithm which analyzes the spectral emission data from the spectrometer and identifies a plurality of optical wavelengths associated with the plasma emission as the wavelengths between a rapid rise in intensity followed by a rapid decline in intensity.

3. The plasma processing system of claim 2 wherein the rapid rise in intensity is defined as being an increase in emission intensity of more than 50 au over a 3 nm change in wavelength.

4. The plasma processing system of claim 2 wherein the algorithm is a data reduction algorithm which produces a second cumulative value for the optical emissions of a second range of wavelengths.

5. The plasma processing system of claim 3 wherein the algorithm is a principal component analysis algorithm which reduces the quantity of optical emission data.

6. The plasma processing system of claim 1, wherein the algorithm is a noise filter which removes noise data from the optical emission data.

7. The plasma processing system of claim 6, wherein the noise filter removes spectral signals that have an intensity of less than about 50 au over a wavelength range of 3 nm.

8. The plasma processing system of claim 1, further comprising:
    a controller for adjusting an operating condition of the plasma processing chamber in response to the plasma processing event being detected by the neural network.

9. A method of plasma processing a substrate, comprising the steps of:
    exposing the substrate to a plasma in a plasma processing chamber;
    monitoring the plasma with a spectrometer which produces plasma emission data;
    processing the plasma emission data with an algorithm to obtain a reduced quantity of plasma emission data by calculating a single cumulative optical intensity representing the cumulative emissions of a range of optical wavelengths associated with a single plasma emission peak; and
    analyzing the reduced quantity of plasma emission data with a neural network to identifying a plasma processing event.

10. The method of plasma processing a substrate of claim 9 wherein the algorithm of the processing step is a peak finding algorithm which removes signals not associated with the plasma emission.

11. The method of plasma processing a substrate of claim 9 wherein the peak finding algorithm identifies a plurality of optical wavelengths associated with the plasma emission as the wavelengths between a rapid rise in intensity followed by a rapid decline in intensity.

12. The method of plasma processing a substrate of claim 11 wherein the rapid rise in intensity is defined as an increase in emission intensity of more than 50 au over a 3 nm change in wavelength and the rapid decline in intensity is defined as a decrease in emission intensity of more than 50 au over a 3 nm change in wavelength.

13. The method of plasma processing a substrate of claim 11 wherein the algorithm in the processing step includes a data reduction algorithm which produces a second cumulative value for the optical emissions of a second range of wavelengths.

14. The method of plasma processing a substrate of claim 9 wherein the algorithm of the processing step is a principal component analysis algorithm.

15. The method of plasma processing a substrate of claim 9 further comprising:
    adjusting an operating condition of the plasma processing chamber in response to identifying a plasma processing event.

* * * * *